United States Patent [19]

Wade et al.

[11] 4,108,860
[45] Aug. 22, 1978

[54] TRIAZOLOBENZISOTHIAZOLE-1,1-DIOXIDES

[75] Inventors: Peter C. Wade, Pennington, N.J.; B. Richard Vogt, Yardley, Pa.; Thomas P. Kissick, Princeton, N.J.

[73] Assignee: E. R. Squibb & Sons, Inc., Princeton, N.J.

[21] Appl. No.: 875,018

[22] Filed: Feb. 3, 1978

[51] Int. Cl.² ............... C07D 275/04; A61K 31/425
[52] U.S. Cl. ............................. 260/304 A; 424/270
[58] Field of Search ....................... 260/304 A, 308 R

[56] References Cited

U.S. PATENT DOCUMENTS

| | | | |
|---|---|---|---|
| 2,751,392 | 6/1956 | Grogan et al. | 260/301 |
| 3,271,406 | 9/1966 | Traverse et al. | 260/301 |
| 3,457,272 | 7/1969 | Crook et al. | 260/301 |

OTHER PUBLICATIONS

Traverso et al, J. Med. Chem., 10(5), 840–844 (1967).
Whitehead et al, J. Med. Chem., 10(5), 845–849 (1967).
Willard et al, J. Med. Chem, 10(5) 849–852 (1967).

*Primary Examiner*—Paul M. Coughlan, Jr.
*Assistant Examiner*—Lisa Jones
*Attorney, Agent, or Firm*—Lawrence S. Levinson; Merle J. Smith

[57] ABSTRACT

New triazolobenzisothiazole-1,1-dioxides which have the formula

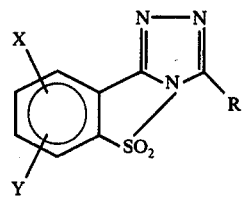

wherein
 R is hydrogen, lower alkyl, phenyl or substituted phenyl;
 X is hydrogen, halogen, lower alkyl, lower alkoxy or nitro; and
 Y is hydrogen, halogen or lower alkoxy,
are useful as anti-inflammatory agents.

7 Claims, No Drawings

TRIAZOLOBENZISOTHIAZOLE-1,1-DIOXIDES

SUMMARY OF THE INVENTION

This invention relates to new triazolobenzisothiazole-1,1-dioxides which have the formula

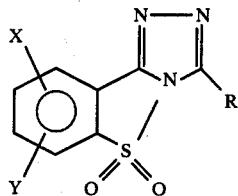

(I)

wherein
R is hydrogen, lower alkyl, phenyl or substituted phenyl wherein the phenyl substituent is halogen, lower alkyl, lower alkoxy or nitro;
X is hydrogen, halogen, lower alkyl, lower alkoxy or nitro; and
Y is hydrogen, halogen or lower alkoxy.

DETAILED DESCRIPTION

The lower alkyl groups represented by the symbols are straight or branched chain aliphatic hydrocarbon radicals having up to 7 carbon atoms, for example, methyl, ethyl, propyl, isopropyl, butyl, isobutyl, t-butyl and the like. The $C_1$–$C_4$ and especially the $C_1$–$C_2$ groups are preferred.

The lower alkoxy groups are also similar groups having up to 7 carbons like methoxy, ethoxy, propoxy, isopropoxy, butoxy, isobutoxy, t-butoxy, etc. The $C_1$–$C_4$ and especially $C_1$–$C_2$ groups are similarly preferred.

The halogens are the four common halogens, chlorine and bromine being preferred in that order.

When Y is other than hydrogen, X represents the same substituent as Y.

The phenyl and subtituted phenyl groups represented by R are substituted and mono-substituted phenyl radicals corresponding to the radical

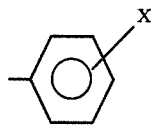

wherein X has the same meaning defined above. Illustrative substituted phenyl groups include o-, m- and p-chlorophenyl, o-, m- and p-bromophenyl, o-, m- and p-methylphenyl, o-, m- and p-ethylphenyl, o-, m- and p-methoxyphenyl, o-, m- and p-nitrophenyl, etc. As above, the $C_1$–$C_4$ and especially $C_1$–$C_2$ lower alkyl and lower alkoxy groups are preferred.

The preferred compounds of formula I are those wherein X and Y are both hydrogen, and R is lower alkyl, especially methyl, or phenyl.

The compounds of formula I, when R is hydrogen or lower alkyl, are produced by reacting a 3-halo-1,2-benzisothiazole-1,1-dioxide having the formula

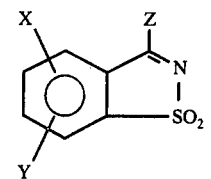

(II)

wherein X and Y have the meanings defined above and Z is halogen, preferably chlorine or bromine, with tetrazole or a 5-alkyltetrazole (produced from an alkyl cyanide like acetonitrile, propionitrile or the like in the presence of ammonium chloride) preferably in the presence of a base like pyridine, lutidine or the like at about room temperature or below.

When R in the product of formula I is phenyl or substituted phenyl, the compounds are preferably produced by first converting the halogenated compound of formula II to a compound having the formula

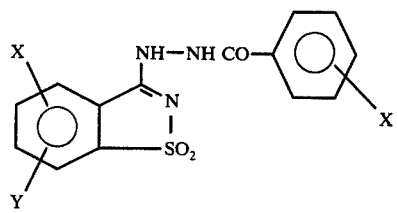

(III)

e.g., by reaction with an unsubstituted or substituted benzoyl hydrazine of the formula

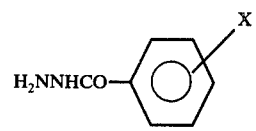

(IV)

and then cyclizing the compound of formula II with a phosphorus halide like phosphorus pentachloride in the presence of a phosphorus oxyhalide like phosphorus oxychloride at an elevated temperature, preferably about reflux temperature.

The starting materials of formula II are produced from saccharin or substituted saccharins which have the formula

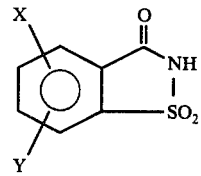

(V)

by reaction with thionyl chloride in an inert organic solvent like dioxane in the presence of dimethylformamide catalyst.

The new compounds of this invention have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally or parenterally in dosages of about 5 to 150 mg/kg/day, preferably 10 to 75 mg/kg/day, in single or 2 to 4 divided doses, as indicated by the Mouse Active Arthus or Delayed Hypersensitivity Skin Reaction assays. The active substance can be utilized in compositions such as tablets, capsules, solutions or suspensions containing up to about 500 mg. per unit of dosage of a compound or mixture of compounds of formula I. They may be compounded in conventional manner with a physiologically acceptable vehicle or carrier, excipient, binder, preservative, stabilizer, flavor, etc. in dosage forms such as those named above containing up to about 500 mg. of active substance as called for by accepted pharmaceutical practice.

The following examples are illustrative of the invention and serve as models for the preparation of additional members by suitable substitution of starting materials. All temperatures are in degrees Celsius.

EXAMPLE 1

3-Methyl-1,2,4-triazolo
[4,3-b][1,2-b]benzisothiazole,5,5-dioxide (a) 100 g (545 mM) of benzisothiazole-1,1-dioxide 100 ml. of thionyl chloride, 4 ml. of dimethylformamide (catalyst) and 400 ml. of dioxane are refluxed overnight. Thionyl chloride (50 ml.) and dimethylformamide (1 ml.) are added to the reaction mixture which is again refluxed overnight. The reaction mixture is evaporated to dryness and the residue recrystallized from toluene to obtain 73.4 g of 3-chloro-1,2-benzisothiazole-1,1-dioxide, m.p. 140°–145°.

(b) 26.0 g (0.4 M) of sodium azide, 21.4 g (0.4 M) of ammonium chloride and 120 ml. of acetonitrile are heated in a pressure bomb in an oil bath at 150° for 25 hours. The resulting solids are filtered off and dissolved in 200 ml. of water. The water is acidified with 40 ml. of concentrated hydrochloric acid and evaporated. The residue is extracted with boiling ethyl acetate (3 × 100 ml). The ethyl acetate is evaporated to yield 31 g. of residue, which is sublimed at 130°/0.2 mm to yield 23.9 g. (68%) of 5-methyltetrazole, m.p. 133°–135°.

(c) 20.0 g. (99.3 mM) of 3-chloro-1,2-benzisothiazole-1,1-dioxide are added to 8.34 g. (99.3 mM) of 5-methyltetrazole dissolved in 200 ml. of dry pyridine. After stirring for 4 hours a precipitate forms which is filtered off, and washed with pyridine and toluene, 15.9 g. (53%). A portion of this material (7.0 g.) is stirred as a suspension in 100 ml. absolute ethanol for 2 hours, filtered off, washed with ethanol, and dried at 40°/vacuum over phosphorus pentoxide overnight to yield 6.2 g. of 3-methyl-1,2,4-triazolo[4,3-b][1,2]benzisothiazole, 5,5-dioxide, compound with pyridine (1:1).

EXAMPLE 2

3-Phenyl-1,2,4-triazolo[4,3-b][1,2]benzisothiazole,5,5-dioxide (a) 6.0 g. (29.8 mM) of 3-chloro-1,2-benzisothiazole, 1,1-dioxide and 4.05 g. (29.8 mM) of benzoylhydrazine are refluxed in 200 ml. toluene for 1 hour. After cooling to room temperature, the precipitate is filtered off and dissolved in 400 ml. ethanol/100 ml. water containing 5 ml. triethylamine. The product is precipitated by the addition of concentrated HCl (to pH 7), filtered, washed with water and alcohol, and dried at 80°/vacuum for 5 hours; yield 6.25 g. benzoic acid, 2-(1,1-dioxo-1,2-benzisothiazol-3-yl)hydrazide, m.p. 289°–290°.

(b) 10.0 g. (33.2 mM) of benzoic acid, 2-(1,1-dioxo-1,2-benzisothiazol-3-yl)hydrazide, 13.8 g (66.4 mM) of phosphorus pentachloride and enough phosphorus oxychloride to cover the solids are refluxed for 3.5 hours. After stirring overnight at room temperature, the resulting precipitate is filtered out, washed with a little phosphorus oxychloride, washed thoroughly with benzene, digested with boiling benzene and filtered to obtain 3.85 g. of 3-phenyl-1,2,4-triazolo[4,3-b][1,2]benzisothiazole, 5,5-dioxide, m.p. 273°–274°.

The following additional compounds having the substituents in the following table (Examples 3 to 17) are produced by the method of Example 1 by substituting for the 3-chloro-1,2-benzisothiazole,1,1-dioxide the 3-chloro-1,2-benzisothiazole-1,1-dioxide having the substituents X and Y in the table, and for the 5-methyltetrazole the tetrazole having substituent R in the table, or by the method of Example 2 by substituting for the benzoic acid, 2-(1,1-dioxide-1,2-benzisothiazol-3-yl)-hydrazide the hydrazide having the R substituent in the table (Examples 18 to 31:

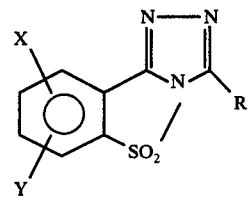

| Example | X | Y | R |
|---|---|---|---|
| 3 | 6-Cl | H | i-C$_3$H$_7$ |
| 4 | 6-Br | H | C$_4$H$_9$ |
| 5 | 7-Br | H | H |
| 6 | 6-Cl | 7-Cl | C$_2$H$_5$ |
| 7 | 8-Cl | 5-Cl | C$_2$H$_5$ |
| 8 | H | H | C$_2$H$_5$ |
| 9 | 6-CH$_3$ | H | H |
| 10 | 6-OCH$_3$ | 7-OCH$_3$ | C$_2$H$_5$ |
| 11 | 6-OCH$_3$ | 7-OCH$_3$ | H |
| 12 | 7-NO$_2$ | H | CH$_3$ |
| 13 | H | H | H |
| 14 | 6-Cl | H | C$_2$H$_5$ |
| 15 | H | H | t-C$_4$H$_9$ |
| 16 | 6-OC$_2$H$_5$ | 7-OC$_2$H$_5$ | CH$_3$ |
| 17 | 7-OCH$_3$ | 8-OCH$_3$ | C$_2$H$_5$ |
| 18 | H | H | —⟨O⟩—Cl |
| 19 | 6-Cl | H | —⟨O⟩ |
| 20 | 7-Br | H | —⟨O⟩—Br |
| 21 | 6-Cl | 7-Cl | —⟨O⟩—Cl |
| 22 | 8-Cl | 5-Cl | —⟨O⟩ |
| 23 | H | H | —⟨O⟩—NO$_2$ |
| 24 | 6-CH$_3$ | H | —⟨O⟩—OCH$_3$ |
| 25 | 6-OCH$_3$ | 7-OCH$_3$ | —⟨O⟩ |
| 26 | 6-OCH$_3$ | 7-OCH$_3$ | —⟨O⟩—OC$_2$H$_5$ |

-continued

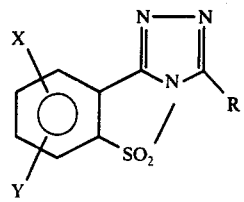

| Example | X | Y | R |
|---|---|---|---|
| 27 | 7-NO$_2$ | H | —C$_6$H$_5$ |
| 28 | H | H | CH$_3$ (2-methylphenyl) |
| 29 | 6-Cl | H | C$_2$H$_5$ (2-ethylphenyl) |
| 30 | H | H | —C$_6$H$_4$—OCH$_3$ |
| 31 | H | H | —C$_6$H$_4$—Br |

What is claimed is:

1. A compound of the formula

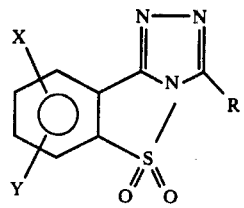

wherein
R is hydrogen, lower alkyl, phenyl or substituted phenyl wherein the phenyl substituent is halogen, lower alkyl, lower alkoxy or nitro; and
X is hydrogen, halogen, lower alkyl, lower alkoxy or nitro; and
Y is hydrogen, halogen or lower alkoxy, with the proviso that when Y is other than hydrogen, X represents the same substituent as Y.

2. A compound as in claim 1 wherein X and Y each is hydrogen.
3. A compound as in claim 1 wherein R is lower alkyl.
4. A compound as in claim 1 wherein R is phenyl.
5. A compound as in claim 2 wherein R is lower alkyl or phenyl.
6. A compound as in claim 2 wherein R is methyl.
7. A compound as in claim 2 wherein R is phenyl.

* * * * *